US00PP37365P2

(12) United States Plant Patent
Esqueda

(10) Patent No.: US PP37,365 P2
(45) Date of Patent: Apr. 7, 2026

(54) ***AGAVE ATTENUATA* PLANT NAMED 'ALTSTARSTRUCK'**

(50) Latin Name: *Agave attenuata*
Varietal Denomination: ALTSTARSTRUCK

(71) Applicant: Altman Specialty Plants llc, Vista, CA (US)

(72) Inventor: Joanne Esqueda, Vista, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/329,308

(22) Filed: Sep. 15, 2025

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/12
See application file for complete search history.

*Primary Examiner* — Kent L Bell

(57) ABSTRACT

A new and distinct cultivar of *Agave* plant named 'ALTstarstruck' is disclosed, characterized by unique and stable variegation throughout the leaves, on both upper and lower surfaces. Foliage of 'ALTstarstruck' has a thick creamy white margin turning into a pale green and green interior color. *Agave* is a popular genus for ornamental purposes, typically produced as large container plants or more commonly as landscape plants.

2 Drawing Sheets

Figure 1:
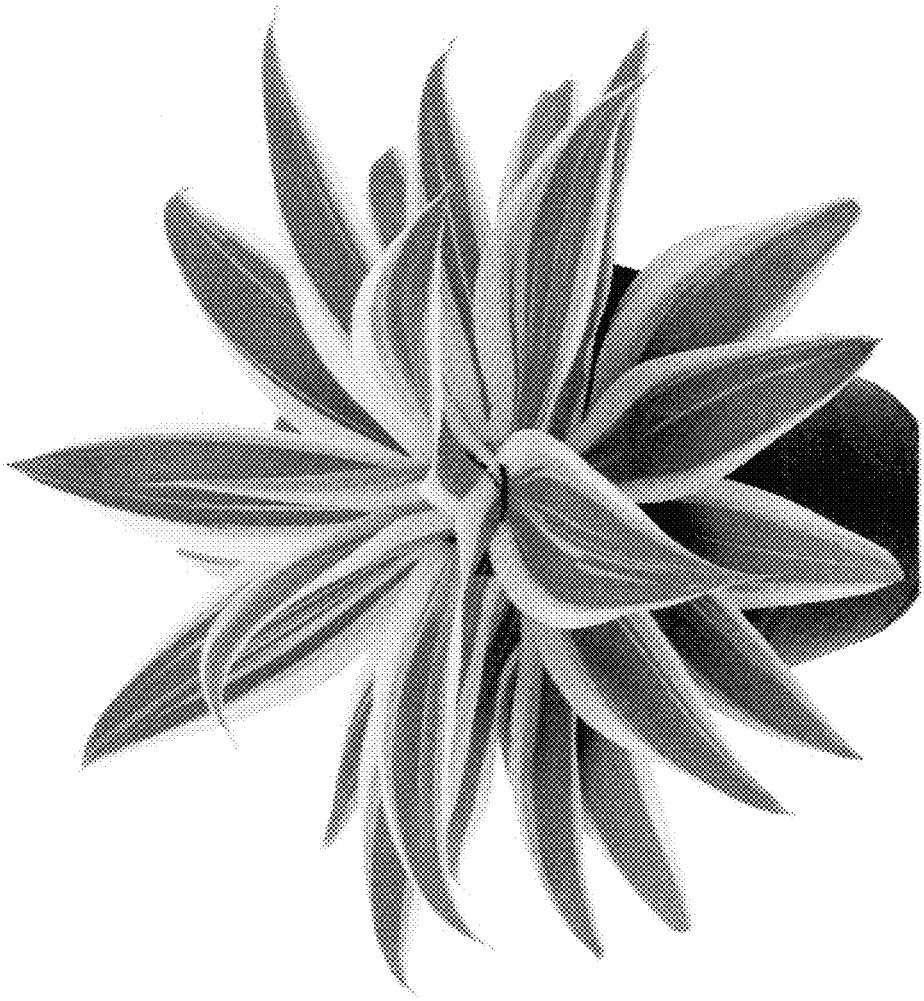

Latin name of the genus and species: *Agave attenuata*.
Cultivar denomination: 'ALTSTARSTRUCK'.

BACKGROUND OF THE INVENTION

The new cultivar, *Agave* 'ALTstarstruck', is the result of chance discovery. The new cultivar was discovered by the inventor as a naturally occurring, whole plant mutation of *Agave attenuata* 'Variegata' (unpatented). The inventor found this interesting mutation among container plantings of the parent variety during 2016 at a commercial nursery in Vista, California.

Asexual reproduction of the new cultivar 'ALTstarstruck' was first performed in Vista, California, at a commercial greenhouse, by vegetative cuttings during the Summer of 2024. 'ALTstarstruck' has since produced multiple generations and has shown that the unique features of this cultivar are stable and reproduced true to type.

SUMMARY OF THE INVENTION

The cultivar 'ALTSTARSTRUCK' has not been observed under all possible environmental conditions. The phenotype may vary somewhat with variations in the environment such as temperature, day length, and light intensity, without, however, any variance in genotype.

The following traits have been repeatedly observed and are determined to be the unique characteristics of 'ALTSTARSTRUCK' These characteristics in combination distinguish 'ALTSTARSTRUCK' as a new and distinct *Agave* cultivar:

1. The new cultivar *Agave attenuata* 'ALTstarstruck' has a unique and stable variegation throughout the leaves, on both upper and lower surfaces.

2. *Agave attenuata* 'ALTstarstruck' has a unique tri color variegation. Foliage has a thick creamy white margin turning into a pale green and green interior color.

PARENTAL COMPARISON

Plants of the new cultivar 'ALTSTARSTRUCK' are similar to plants of the parent in most horticultural characteristics, however, plants of the new cultivar 'ALTSTARSTRUCK' differ in the following;

1. *Agave attenuata* 'ALTstarstruck' has a much thicker creamy white margin than the parent variety.
2. *Agave attenuata* 'ALTstarstruck' has consistent variegation on both upper and lower surfaces; the parent variety is inconsistent in its foliar variegation and often has no variegation on the lower leaf surface.

COMMERCIAL COMPARISONS

Plants of the new cultivar 'ALTSTARSTRUCK' are comparable to the commercial cultivar *Agave attenuata* 'Kara's Stripes', U.S. Plant Pat. No. 19,444. The two *Agave* cultivars are similar in most horticultural characteristics; however, the new cultivar 'ALTSTARSTRUCK' differs in the following:

1. Foliage of *Agave attenuata* 'ALTstarstruck' is more consistently variegated, producing a similar pattern on both upper and lower foliage.
2. Foliage of 'Kara's Stripes' is predominantly cream yellow with yellow-green or grey-green narrow bands along the leaf edge. Foliage of *Agave attenuata* 'ALTstarstruck' has a thick creamy white margin turning into a pale green and green interior color.

Plants of the new cultivar 'ALTSTARSTRUCK' can also be compared to an unpatented, unnamed *Agave attenuata* found in the horticultural market. The two *Agave* cultivars are similar in most horticultural characteristics; however, the new cultivar 'ALTSTARSTRUCK' differs in the following:

1. *Agave attenuata* 'ALTstarstruck' has variegated foliage, whereas the unnamed *Agave attenuata* has solid green foliage.
2. *Agave attenuata* 'ALTstarstruck' is about 20% to 30% more compact growing than the unnamed *Agave attenuata*, which has a lankier morphology.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new cultivar *Agave* 'ALTstarstruck'.

The accompanying photograph in FIG. 1 illustrates in full color a plant of *Agave* 'ALTstarstruck', at about 15 months, grown at a nursery (approximately 2500 foot candles) in Vista, California in 5-gallon pot.

Figure 2:
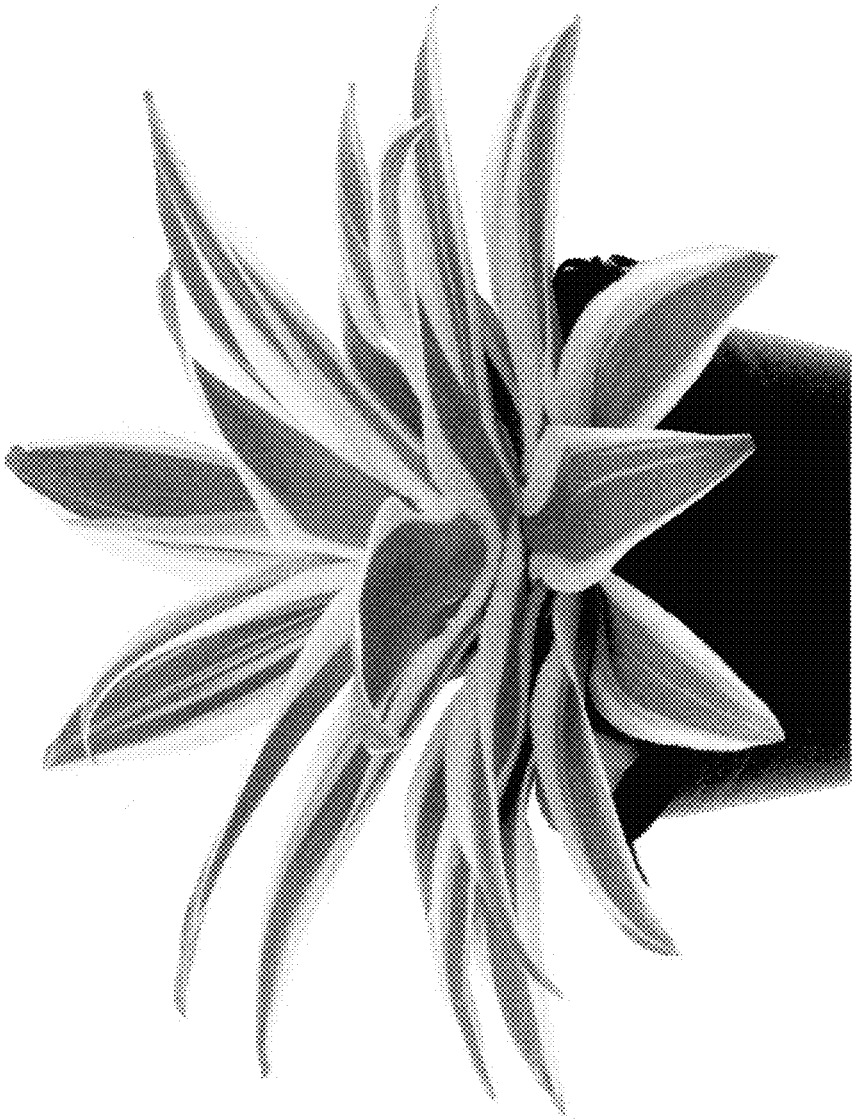

FIG. 2 is a slightly different view of the same plant, showing the underside of the leaves.

DETAILED BOTANICAL DESCRIPTION

In the following description, color references are made to The Royal Horticultural Society Colour Chart, 2015 edition, except where general terms of ordinary dictionary significance are used. The following observations and measurements describe 'ALTstarstruck' plants grown in a commercial nursery in Vista, California. Temperatures ranged from about 34° F. to 90° F. No artificial light, photoperiodic treatments or chemical treatments were given to the plants. Natural light conditions were approximately 2500 to 3000 fc of light. Measurements and numerical values represent averages of typical plant types.

Botanical classification: *Agave attenuata* 'ALTstarstruck'.

PROPAGATION

Type of propagation typically used: Terminal vegetative cuttings.

Time to initiate roots: About 25 to 45 days at approximately 25° C.

Root description: Woody main roots producing fibrous laterals. Main roots colored Greyed-Orane 177A. Laterals colored 159C and 177D.

PLANT

Age of plant described: Approximately 15 months.

Container size of the plant described: 5 gallon pot.

Growth habit: Non-branching rosette. Additional rosettes (pups) produced basally.

Height: Approximately 32 cm.

Plant spread: Approximately 58 cm.

Branching characteristics: None.

Main stem: Not visible. Leaves tightly arranged in central rosette.

FOLIAGE

Leaf:

*Arrangement*.—Rosette.

*Quantity of leaves per plant*.—30 to 35.

*Average length*.—Approximately 24 to 30 cm.

*Width*.—7-8 cm.

*Depth*.—2 mm.

*Shape of blade*.—Lanceolate.

*Apex*.—Acute.

*Base*.—Clasping.

*Margin*.—Entire.

*Texture of top surface*.—Glabrous.

*Texture of bottom surface*.—Glabrous. Very slightly glaucous.

*Leaf internode*.—No internode, leaves overlapping in rosette.

*Color*.—Young foliage upper side: Center RHS Green 138B and 137D, streaked together. Thick (8 mm to 1 cm) margins White 155B flushed yellow 2D. Margin fades to Green 138D. Young foliage, under side: Center RHS Green 138B and 137D, streaked together. Thick (8 mm to 1 cm) margins White 155B flushed yellow 2D. Margin fades to Green 138D. Mature foliage upper side: Center RHS Green 138B and 137D, streaked together. Thick (8 mm to 1 cm) margins White 155B. Margin fades to Green 138D. Mature foliage under side: Center RHS Green 138B and 137D, streaked together. Thick (8 mm to 1 cm) margins White 155B. Margin fades to Green 138D.

*Venation*.—Indistinguishable from leaf blade.

FLOWER

Flowering not observed to date.

REPRODUCTIVE ORGANS

Unknown, flower has not yet been observed.

OTHER CHARACTERISTICS

Fruits and seeds: Unknown; has not flowered to date.

Temperature tolerance: USDA Zones 9-11.

Disease/pest resistance: Neither resistance nor susceptibility to diseases and pests of *Agave* has been observed.

Drought tolerance: Can tolerate near total drought once established.

What is claimed is:

1. A new and distinct cultivar of *Agave* plant named 'ALTstarstruck' as herein illustrated and described.

* * * * *